United States Patent [19]

Machida et al.

[11] Patent Number: 5,133,087

[45] Date of Patent: Jul. 28, 1992

[54] LAMINATE HAVING INDICATOR FUNCTION

[75] Inventors: Morihisa Machida, Hayama; Yoshio Tajima, Ito; Hideo Nakatsumi, Ichikawa; Tatsuo Isahai, Takasaki; Daijiro Shiroki, Nagareyama, all of Japan

[73] Assignees: The Yokohama Rubber Co., Ltd.; Hitachi, Ltd., both of Tokyo, Japan

[21] Appl. No.: 629,852

[22] Filed: Dec. 18, 1990

Related U.S. Application Data

[62] Division of Ser. No. 243,559, Aug. 5, 1988, Pat. No. 5,017,427.

[30] Foreign Application Priority Data

Dec. 8, 1986 [JP] Japan ................... 61-290530
Dec. 7, 1987 [WO] PCT Int'l Appl. ............ 87/00945

[51] Int. Cl.⁵ ............................................. A41D 19/00
[52] U.S. Cl. ............................................. 2/168; 2/167
[58] Field of Search ................... 128/917, 918, 919; 2/167, 168, 161 R, 159, 164, 163; 428/323, 518, 913

[56] References Cited

U.S. PATENT DOCUMENTS

| 4,843,014 | 6/1989 | Cukier | 2/168 X |
| 4,910,803 | 3/1990 | Cukier | 128/918 X |
| 4,935,260 | 6/1990 | Shlenker | 2/168 X |
| 4,935,308 | 6/1990 | Guerra et al. | 2/159 X |
| 4,992,335 | 2/1991 | Guerra et al. | 2/159 X |
| 5,017,427 | 5/1991 | Machida et al. | 2/168 X |

FOREIGN PATENT DOCUMENTS

| 3925938 | 4/1990 | Fed. Rep. of Germany | 2/168 |
| 2208358 | 3/1989 | United Kingdom | 2/159 |
| 90/03632 | 4/1990 | World Int. Prop. O. | 2/164 |

Primary Examiner—Werner H. Schroeder
Assistant Examiner—Sara M. Current
Attorney, Agent, or Firm—Nikaido, Marmelstein, Murray & Oram

[57] ABSTRACT

A laminate comprising an inner layer containing an acid/base indicator and an outer layer containing no acid/base indicator, wherein the inner layer is capable of undergoing a color change upon its contact with an acid or an alkali.

5 Claims, No Drawings

LAMINATE HAVING INDICATOR FUNCTION

This is a division, of application Ser. No. 07/243,559 filed Aug. 5, 1988.

DESCRIPTION

1. Field of Art

The present invention relates to a laminate which includes an inner layer imparted with a function to change its color upon its contact with acid or alkali and which is in the form of, for example, working gloves.

2. Background Art

In the manufacture of electronic parts and elements such as semi-conductor devices and so forth, a variety of chemicals such as an acid, an alkali, a solvent and so forth are used in various treatment operations, starting with deburring of substrates and surface washing.

In carrying out such operations, conventionally it has been practiced to make use of working gloves made of material of a laminate structure, comprising rubber or a resin having a rubber elasticity and a remarkable chemical resistance. However, the treatment operations deal with strongly harmful chemicals such as a strong acid and a strong alkali, so that the entry of a chemical into the gloves contacted with the chemical, if occurs through any breakage in the gloves, tends to result in a serious accident. Therefore, measures are taken, for example such as to carry out an inspection to locate any breakage in the gloves by a pinhole finding test or to discard used gloves as waste after the lapse of the prescribed length of time of use of the gloves regardless of the possibility that the gloves can still stand use.

In the above circumstances, it has been strongly desired in the art to develop such gloves having a laminate structure which have a high degree of safety and are economical.

The present invention has been made in order to obviate the above indicated problems in the art, and is directed in its object to provide a laminate which internally includes a layer capable of undergoing a color change in contact with an acid or an alkali (hereinafter referred to as a color indicator layer) and thereby detecting permeation of the acid or alkali into the laminate. According to the present invention, it is feasible to provide gloves having a laminate structure imparted with a detecting function as above, which are relatively thin and can be used at safety and using which operations can be facilitated.

DISCLOSURE OF THE INVENTION

To attain the above object, the laminate having an indicator function according to the present invention is characterized by comprising an inner layer and an outer layer, of which the inner layer contains a chemical acid/base indicator.

BEST MODE FOR CARRYING OUT THE INVENTION

Now, a detailed description will be given the constitutional features of the present invention.

(1) Outer Layer

Preferably, the outer layer should have a transparency so that a color change of an underlying color indicator layer can be visually ascertained and, in addition, have a resistance to an acid and an alkali. This outer layer is not necessarily required to comprise a single layer, but it may comprise a plurality of layers comprising different material or having different characteristics, as needs be.

Although no particular limitation is applied to the material for the outer layer, since this layer is subjected to a direct contact with an acid or an alkali, it is advantageous to make use of such material as having a remarkable resistance to acid and alkali. For example, such as chlorosulfonated polyethylene, chlorinated polyethylene and butyl rubber are suitably useful, but it is also feasible to use any other rubber or resin, if required.

(2) Inner Layer

The inner layer, which lies next to an outer layer or outer layers as above, consists in a layer containing a chemical acid/base indicator, namely a color indicator layer which has a function to present a color change upon its contact with an acid or an alkali tending to migrate into this layer through any breakage in the outer layer or layers.

A chemical acid/base indicator of a suitable color changing characteristic (a pH range) may be selectively determined and employed for use, in consideration of the pH value of the particular acid or alkali with which the laminate is supposed to be contacted. For a useful indicator, for example such as a phenolphthalein, methyl orange and congo red may be named. The compounding amount of the indicator may be such that the indicator presents a color change which can be detected, and it may be for example within a range of 0.5 to 1.5 parts by weight to 100 parts by weight of rubber or resin which forms the color indicator layer.

The color indicator layer is not necessarily required to comprise a single layer but may comprise a plurality of layers. Where the color indicator layer comprises a plurality of layers, it is feasible to vary the chemical acid/base indicator between or among the layers.

For the material for the color indicator layer, a suitable rubber or resin may be selectively employed for use.

Further, for example where the safety in use is particularly required depending on the utility of the laminate, it may be devised to provide next to or inner to the color indicator layer, a further layer comprising a rubber or resin having a resistivity to acid and alkali. In this case, it is feasible to effectively avoid a danger even if the color indicator layer is wholly destroyed.

The rubber or resin for use for the color indicator layer and a further layer which may be possibly laminated next to or inner to the color indicator layer as needs be is not limited to any particular one, and it may be appropriately selected for use in consideration of conditions under which the laminate is used.

When necessary, further, such as a crosslinking agent, a filler, a dispersing agent and so forth may be blended in the rubber or resin used for the outer layer and any other layer or layers.

Examples will be shown below.

EXAMPLES

In nitrile rubber (a latex was used and a crosslinking agent was added), various acid/base indicators as shown in the below Table 1 were blended, and the resulting mixture was dried and solidified to provide films for the color indicator layers, on which a film of chlorosulfonated polyethylene (a latex was used and a crosslinking agent was added) was formed. The resulting laminates were subjected to a heat-treatment at 140° C. for 30 minutes to obtain sheets of a two-layer structure. Then, an incision of a depth reaching the color indicator layer was applied to each sheet and an acid solution was dropwise applied at the location of the incision to determine the characteristic and the speed of changing of colors as a result of the contact of the color indicator layer with the acid, and the visibility of the color change through the outer layer.

The below Table 1 also shows the results of the determinations made.

TABLE 1

| Outer Layer | Chlorosulfonated Polyethylene | | | | | |
|---|---|---|---|---|---|---|
| Color Indicator Layer | Acrylonitrile-Butadiene Rubber Latex | | | | | |
| Acid/base Indicator | Methyl Orange | | | Congo Red | | |
| Acid | Sulfuric Acid | Nitric Acid | Hydrochloric Acid | Sulfuric Acid | Nitric Acid | Hydrochloric Acid |
| Colour Change | | | | | | |
| Before contact with acid | Orange | Orange | Orange | Red | Red | Red |
| After contact with acid | Red | Red | Red | Violet | Violet | Violet |
| Colour Change Speed | immediately changed from orange to pale red, and then to clear red | | | immediately changed from red to violet | | |
| Visibility | Good | Good | Good | Good | Good | Good |

As seen from the above Table 1, the color indicator layer containing methyl orange or congo red, an acid/base indicator, underwent a clear color change upon its contact with each of sulfuric acid, nitric acid and hydrochloric acid, and also the visibility of the color change through the outer layer was satisfactory, the color change being fully ascertainable, visually.

CAPABILITY OF EXPLOITATION OF THE INVENTION IN INDUSTRY

As stated above, according to the present invention a color indicator layer is provided in a laminate and thereby it is feasible to attain the following effects/results.

(1) With the laminate according to the invention, a layer provided next to or inner to an outer layer having a chemical resistance is imparted with a function to present a color change upon its contact with an acid or an alkali, so that permeation of an acid or alkali through a breakage in the outer layer can be visually detected, whereby the safety in operations can be greatly enhanced.

(2) Since it can be perceived as a change in color, the generation of any breakage in the laminate can be detected with ease and without fail, so that it is feasible to manufacture gloves of a reduced thickness in comparison to conventionally produced gloves, whereby with use of the gloves made of a laminate according to the invention, various operations can be more easily performed.

(3) The degree of a damage of the laminate can be told by the degree of a color change in or of the color indicator layer, so that an economical advantage can be brought about in that the need in the prior art is no longer applicable, of having to discard gloves as waste after the lapse of the prescribed length of use time regardless of the possibility that the gloves can still stand the use in actuality.

(4) Also attributable to the above fact that the degree of a damage in the laminate can be told by the degree of a color change in the color indicator layer, an economization can be realized of the time and the cost required for an inspection in that the conventionally indispensable pinhole finding tests can now be done without.

(5) The laminate according to the present invention has a wide range of utility in addition to its application to gloves, for various goods such as a lining material, a covering material for machines and implements and so forth.

We claim:

1. A thin working glove for use in the production of electronic parts and elements comprising a laminate having a function of an indicator, the laminate comprising an acrylonitrile-butadiene rubber inner layer which contains an acid/base indicator which changes color upon contact with acid or an alkali and an outer layer of a material selected from the group consisting of chlorinated-polyethylene, chlorosulfonated polyethylene and butyl rubber, said outer layer being adapted to be furthest away from the wearer.

2. A glove as claimed in claim 1, wherein said acid/base indicator is phenolphthalein, methyl orange or Congo red.

3. A glove as claimed in claim 1, wherein said inner layer comprises a plurality of layers each containing a different acid/base indicator.

4. A glove as claimed in claim 1 wherein said inner layer has been made by blending said acid/base indicator with a latex of said acrylonitrile-butadiene rubber; and solidifying said blend by drying.

5. A glove as claimed in claim 1 containing 0.5 to 1.5 parts by weight of said indicator per 100 parts by weight of said acrylonitrile-butadiene rubber.

* * * * *